(12) United States Patent
Gerbershagen et al.

(10) Patent No.: US 10,463,881 B2
(45) Date of Patent: Nov. 5, 2019

(54) PARTICLE THERAPY GANTRY WITH AN ENERGY DEGRADER AND AN ACHROMATIC FINAL BENDING SYSTEM

(71) Applicant: PAUL SCHERRER INSTITUT, Villigen PSI (CH)

(72) Inventors: Alexander Gerbershagen, Brugg (CH); David Meer, Brugg (CH); Jacobus Maarten Schippers, Remigen (CH)

(73) Assignee: Paul Scherrer Institut, Villigen PSI (CH)

( * ) Notice: Subject to any disclaimer, the term of this patent is extended or adjusted under 35 U.S.C. 154(b) by 0 days.

(21) Appl. No.: 15/776,478

(22) PCT Filed: Oct. 28, 2016

(86) PCT No.: PCT/EP2016/076099
§ 371 (c)(1),
(2) Date: May 16, 2018

(87) PCT Pub. No.: WO2017/084864
PCT Pub. Date: May 26, 2017

(65) Prior Publication Data
US 2018/0369612 A1    Dec. 27, 2018

(30) Foreign Application Priority Data
Nov. 16, 2015   (EP) .................................. 15194795

(51) Int. Cl.
*A61N 5/10* (2006.01)
*H05H 7/04* (2006.01)
*H05H 7/00* (2006.01)

(52) U.S. Cl.
CPC ......... *A61N 5/1043* (2013.01); *A61N 5/1081* (2013.01); *A61N 5/1082* (2013.01);
(Continued)

(58) Field of Classification Search
CPC .. A61N 5/1043; A61N 5/1081; A61N 5/1082; A61N 2005/1087; H05H 7/04;
(Continued)

(56) References Cited

U.S. PATENT DOCUMENTS 6,814,694 B1   11/2004   Pedroni
7,348,579 B2    3/2008   Pedroni
(Continued)

FOREIGN PATENT DOCUMENTS

DE   102007032025 A1   12/2008
JP      2000202047 A    7/2000
(Continued)

*Primary Examiner* — Nicole M Ippolito
(74) *Attorney, Agent, or Firm* — Laurence Greenberg; Werner Stemer; Ralph Locher

(57) ABSTRACT

A movable gantry for delivery of a particle beam using beam scanning technique contains an inlet section for an accelerated particle beam having quadrupole magnets, first and second bending sections having dipole and quadrupole magnets for beam correction, a transfer section having quadrupole magnets for beam correction and a degrader and a last beam bending section having separate and/or combined dipole/quadrupole/higher order multipole magnets forming an achromatic section. All the magnets of the achromatic last bending section are located downstream of the degrader. Any dispersion in this achromatic last bending section is suppressed. A scanning section having two separate or one combined fast deflection magnets that deflect the beam at the iso-center in a direction perpendicular to the beam direction to perform lateral scanning is provided. A beam nozzle section is provided and has a beam nozzle.

7 Claims, 6 Drawing Sheets

(52) U.S. Cl.
CPC ....... *H05H 7/04* (2013.01); *A61N 2005/1087* (2013.01); *H05H 2007/002* (2013.01); *H05H 2007/004* (2013.01); *H05H 2007/045* (2013.01); *H05H 2007/048* (2013.01)

(58) Field of Classification Search
CPC ....... H05H 2007/002; H05H 2007/004; H05H 2007/045; H05H 2007/048
USPC ........................ 250/396 R, 397, 492.1, 492.3
See application file for complete search history.

(56) References Cited

U.S. PATENT DOCUMENTS

| | | | | |
|---|---|---|---|---|
| 2011/0101236 | A1* | 5/2011 | Cameron | A61N 5/1077 250/396 ML |
| 2012/0280150 | A1* | 11/2012 | Jongen | A61N 5/10 250/492.3 |
| 2014/0171725 | A1 | 6/2014 | Adler et al. | |
| 2016/0247591 | A1* | 8/2016 | Bromberg | G21K 1/093 |
| 2017/0372867 | A1* | 12/2017 | Caspi | H01F 41/048 |
| 2018/0326226 | A1* | 11/2018 | Ebina | A61N 5/1081 |

FOREIGN PATENT DOCUMENTS

| | | |
|---|---|---|
| JP | 2013508646 A | 3/2013 |
| JP | 2013509277 A | 3/2013 |

\* cited by examiner

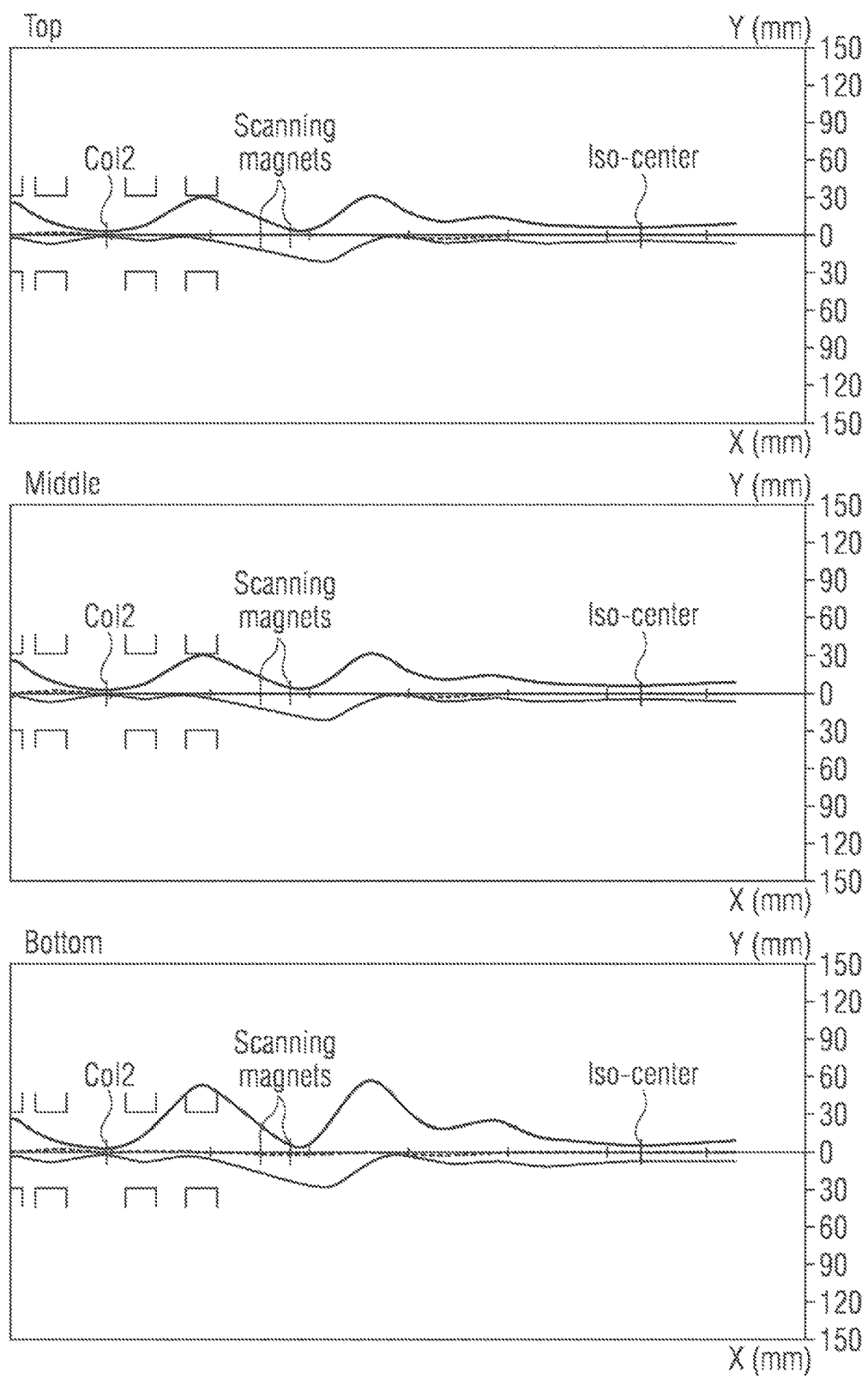

PARTICLE THERAPY GANTRY WITH AN ENERGY DEGRADER AND AN ACHROMATIC FINAL BENDING SYSTEM

BACKGROUND OF THE INVENTION

Field of the Invention.

The present invention relates to a gantry for fast-scanning delivery of a particle beam, for example for cancer treatment in human tissue, using a proton or a carbon or helium ion beam. What is presented here for proton beams, is also applicable for any other ion beam, such as those of carbon or helium.

In proton therapy the Bragg peak (high dose peak) occurring just before the end of the proton range in tissue is used to deposit a high dose in the target tissue while preventing a too high dose in healthy tissue. In the scanning pencil beam technique, a narrow proton beam is scanned in the two transverse directions and the depth of the Bragg peak is set by adjusting the energy of the pencil beam.

The size of the tumor projection in the plane perpendicular to the beam direction is usually much larger than the beam diameter. Scanning of the beam in both transverse directions is performed via the deflection of the narrow 'pencil beam', a technique first demonstrated in NIRS (see FIG. 2) and LBNL and clinically first used on a gantry at PSI (see FIG. 4 top). The beam is deflected via the scanning magnets, which are usually located before (upstream scanning) or behind (downstream scanning) the final bending magnet in the gantry, but also other possibilities exist.

The depth location of the Bragg is set by choosing the beam energy (momentum). Given the width of the Bragg peak, spreading the dose over the tumor thickness is performed by shifting the Bragg peak over the tumor thickness in steps of approx. 5 mm. The corresponding required change of the momentum per layer is of the order of ~1%, approximately corresponding to an energy change of 0.5%. This step size depends on the particle type and for carbon ions this can typically be a factor 2 less.

Presently, in many of the operating proton therapy facilities the beam is accelerated by a cyclotron with fixed extraction energy. In cyclotron facilities the energy is reduced to the required value by a so-called degrader—an insertion of low Z material in the beam transport system—. Such a system and the following magnets should be designed such that energy variations are made as fast as possible when spreading the dose in depth over the tumor thickness.

In order to limit the treatment time, it is useful not to lose too much time by waiting until an energy change is made for depth variation of the pencil beam. This will be discussed in more detail later in this document.

A gantry is a mechanical rotatable construction, supporting the beam transport system at the final sections of the proton therapy facility beam lines. Its beam transport system is composed of several dipole and quadrupole magnets, which are able to bend proton beams with a maximum energy of approximately 230-250 MeV or carbon ions of approximately 450 MeV/nucl. Its rotation together with the movement of the patient table allows irradiating the tumor tissue from different directions, as for example disclosed in the U.S. Pat. Nos. 6,814,694 and 7,348,579. The so-called iso-center is the common point in space, where the gantry rotational axis is crossed by the beams from all gantry directions. The scanning system deflects the beam in a lateral direction with respect to the direction of the central (non-scanned) beam that is aiming at the iso-center.

The bending of the beam trajectory in every dipole magnet causes the particles with a non-nominal momentum to deviate their trajectory from the nominal axis of the beam. This chromatic phenomenon is called dispersion and is usually described by the so called dispersion function, indicating the deviation from the optical axis of the trajectory of a particle with usually 1% momentum offset. The combination of gantry magnet apertures and the maximum amplitude of this trajectory determines the maximum momentum deviation that can be accepted by the gantry. Most of the existing gantries accept a momentum band of about ±0.5 to 1% due to a so called chromatic correction.

In this document two types of so called achromatic systems are distinguished.

A global achromatic system suppresses the transverse and angular dispersion of the beam at the iso-center.

A system with local achromaticity performs dispersion suppression by a subgroup of magnets within the gantry.

Using local or global achromatic systems ensures that the beam position is independent of energy after traversing such a system. In existing gantries usually a global chromatic correction is applied.

When the energy (momentum) of the beam is changed by more than the momentum acceptance of the gantry, all gantry magnets must be adjusted accordingly, otherwise beam will be lost in the gantry. This is normally the case, since several energy steps of approximately 2% need to be made to cover a typical tumor thickness.

In 2011 a design of a superconducting gantry for proton therapy has been proposed by ProNova (see FIG. 1). This design consists of two bending sections. The optics of each bending section has been designed such that it is locally achromatic. This gantry is commercially available, but no clinically working system is in operation at the moment of writing. In 2012 and based on this gantry, a gantry has been designed for 350 MeV protons at PSI. This gantry design shows ±3% momentum acceptance, enabled by the locally achromatic bending sections. This already large momentum acceptance was considered as an advantage for the plans to implement a linear accelerator before the gantry. In the way it was planned to be applied, it would cause a too large momentum spread for conventional gantry designs, but acceptable for the PSI design.

SUMMARY OF THE INVENTION

Therefore, a gantry for particle therapy with a large momentum acceptance is one of the objectives of the present invention.

This objective is achieved according to the present invention by a movable gantry for delivery of a particle beam using beam scanning technique, for example for the cancer treatment in human tissue; comprising:

a) an inlet section for an accelerated particle beam comprising a number of quadrupole magnets;

b) a first bending section and optionally a second bending section comprising a number of dipole and quadrupole magnets and optionally further magnets for beam correction;

c) a transfer section comprising a number of quadrupole magnets and optionally further magnets for beam correction and a degrader;

d) a last beam bending section comprising a number of separate and/or combined dipole/quadrupole/higher order multipole magnets forming an achromatic section, wherein all magnets of this achromatic last bending section are located downstream of the degrader; any dispersion in this achromatic last bending section is suppressed so that it will have a momentum acceptance of more than ±5%;

e) a scanning section comprising two separate or one combined fast deflection magnets that deflect the beam at the iso-center in a direction perpendicular to the beam direction to perform lateral scanning; and f) a beam nozzle section comprising a beam nozzle and optionally beam handling equipment, such as further beam degrading or modifying elements and/or beam quality related beam verifying elements.

Assuming that the last bending system of the gantry has local achromaticity with sufficient momentum acceptance, the second part of the invention is to couple this feature to a degrader mounted in the gantry, at a location before the last bending system. The energy of the beam entering the patient is set by the degrader. The beam optics, comprising of the settings of the magnets and collimation systems, of the following system(s) is designed such that the combination of:

the energy of the beam behind the degrader (within a certain range)

the momentum spread caused by the degrader the deflection of the beam by eventual scanning magnets before or in the bending system emittance limitation by the collimator(s) following the degrader does not lead to beam losses in the bending system.

The degrader is preceded by a collimator to control the beam size and beam location at the degrader entrance. The degrader is followed by a collimation system to control the beam emittance behind the degrader to a value that is matching the beam to the acceptance of the following magnets in the gantry systems and to adjust the cross section of the pencil beam at the exit of the gantry.

By using local achromatic bending section(s), the momentum acceptance of the gantry according to the present invention can be made much larger than in global achromatic systems, for example +/−15%. Therefore, a second objective reached with this invention is that the magnets in the gantry according to the present invention do not have to change their field when the beam energy changes. Many tumor thicknesses can then be covered with one magnetic field setting. The time it takes to make an energy change is then determined by the mechanics of a degrader system before the local achromatic bend and by some small energy-dependent corrections of focusing magnets.

In preferred embodiments of the gantry, the scanning section can be positioned upstream or within or downstream of the last beam bending section. Further, a collimator or collimator system can be positioned downstream of the degrader.

In order to allow an access to a patient table being positioned in the iso-center of the gantry also during the delivery of the particle therapy, the gantry can be oriented by means of a (combination of) rotation or a shift, of one or more parts of the last section(s) of the beam transport line.

Other preferred embodiments of the present invention are listed in the depending claims.

BRIEF DESCRIPTION OF THE SEVERAL VIEWS OF THE DRAWING

Preferred embodiments of the present invention are described hereinafter with reference to the attached drawings which depict in:

FIG. 6 the beam optics of the gantry after the collimation point Col2 for the following three cases:

Top: magnets set at the value corresponding to the beam momentum,

Middle: magnets set at 10% more than the value corresponding to the beam momentum and Bottom: magnets set at 10% more than the value corresponding to the beam momentum and with a beam divergence of 21 mrad at Col2.

DESCRIPTION OF THE INVENTION

A possible option for a beam optics design of a gantry based on the requirements specified above has been developed and is described in more detail in the following.

Figure 1:
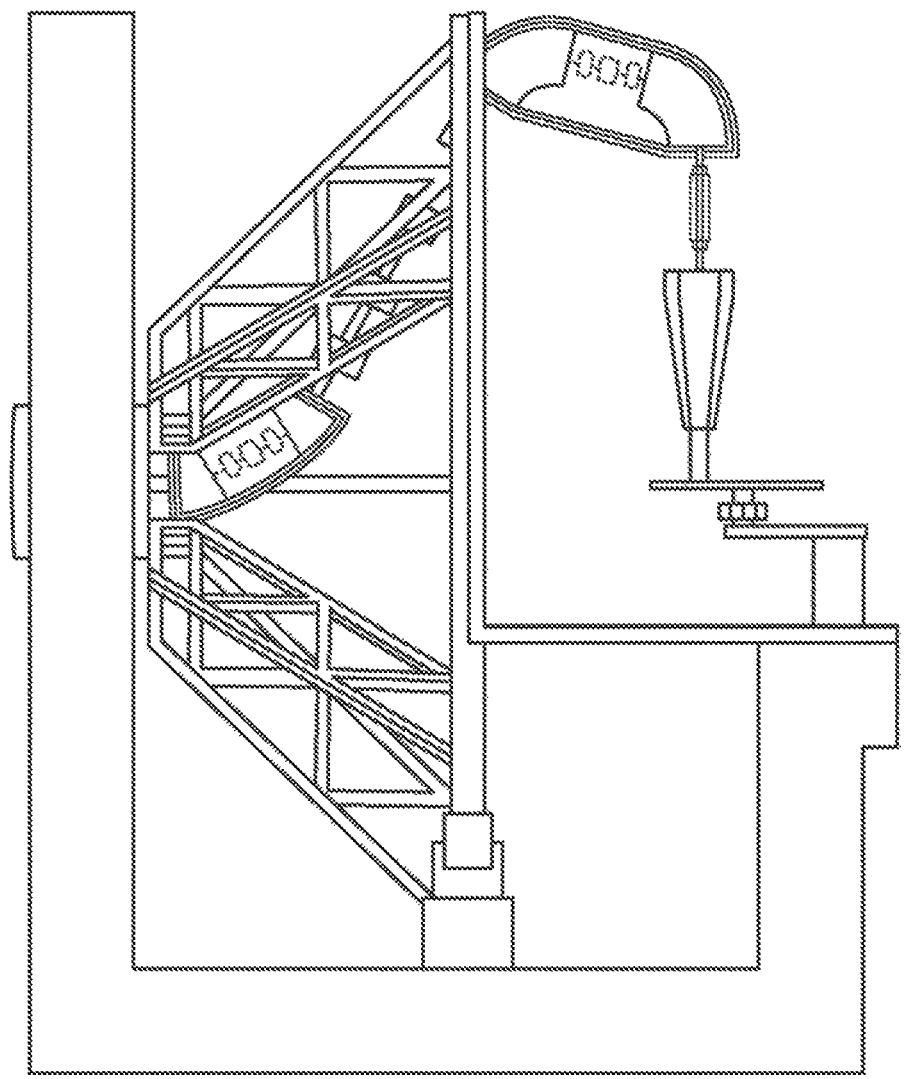
FIG. 1 schematically the layout of the ProNova superconducting SC360 Gantry.
Figure 2:
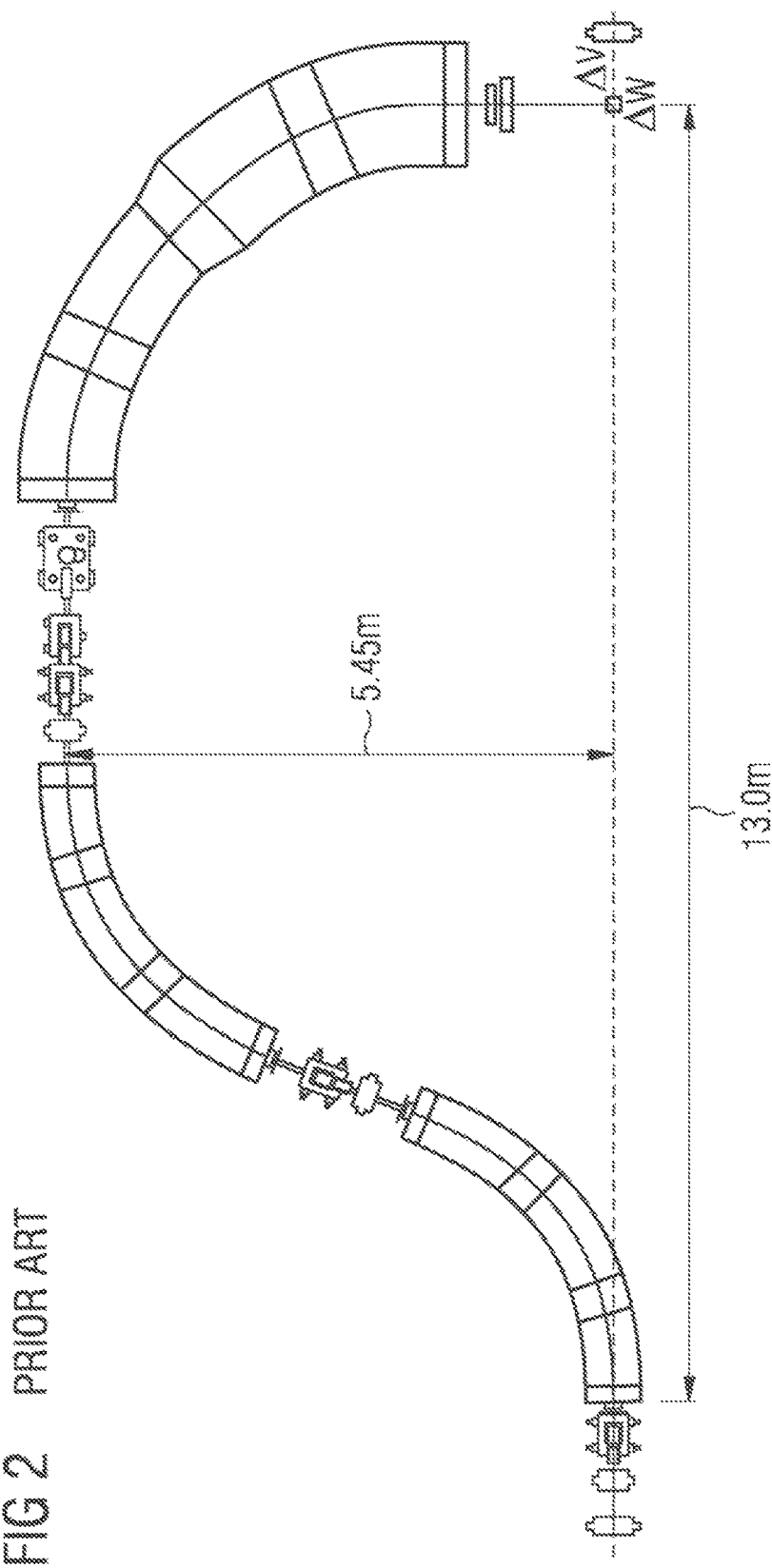
FIG. 2 schematically the layout of a NIRS superconducting carbon ion gantry.
Figure 3:
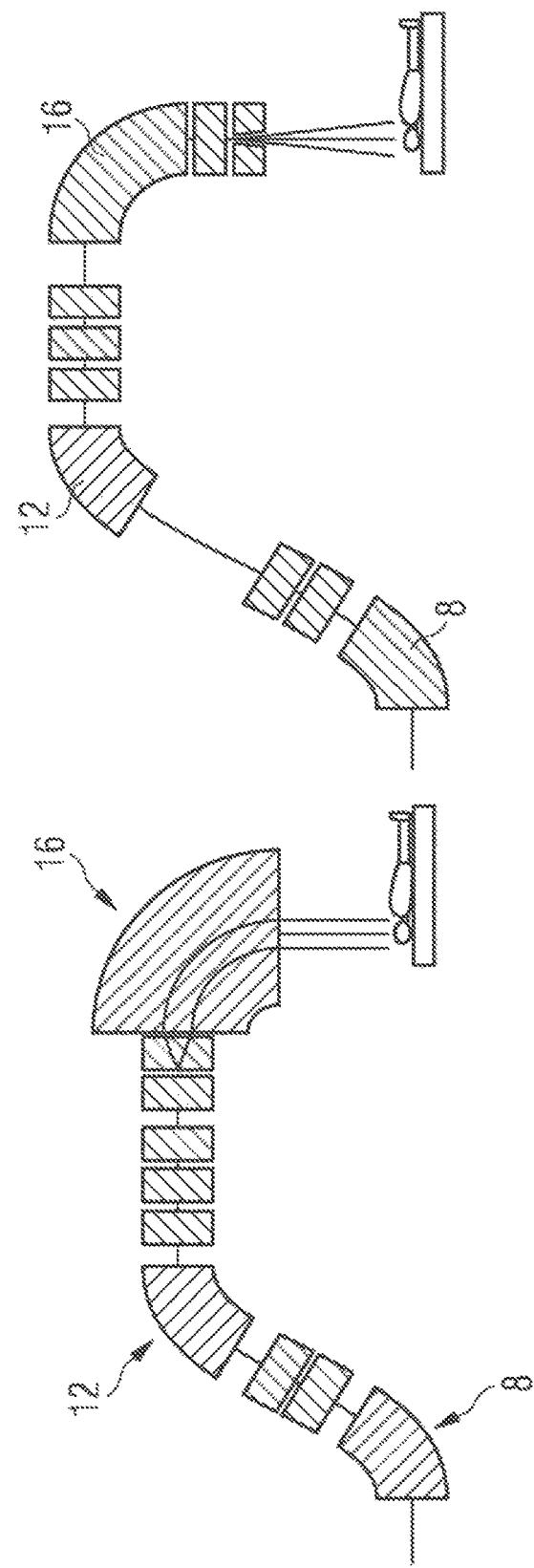
FIG. 3 schematically the layout of scanner magnets being located upstream (left) or downstream (right) of the final bending magnet.
Figure 4A:
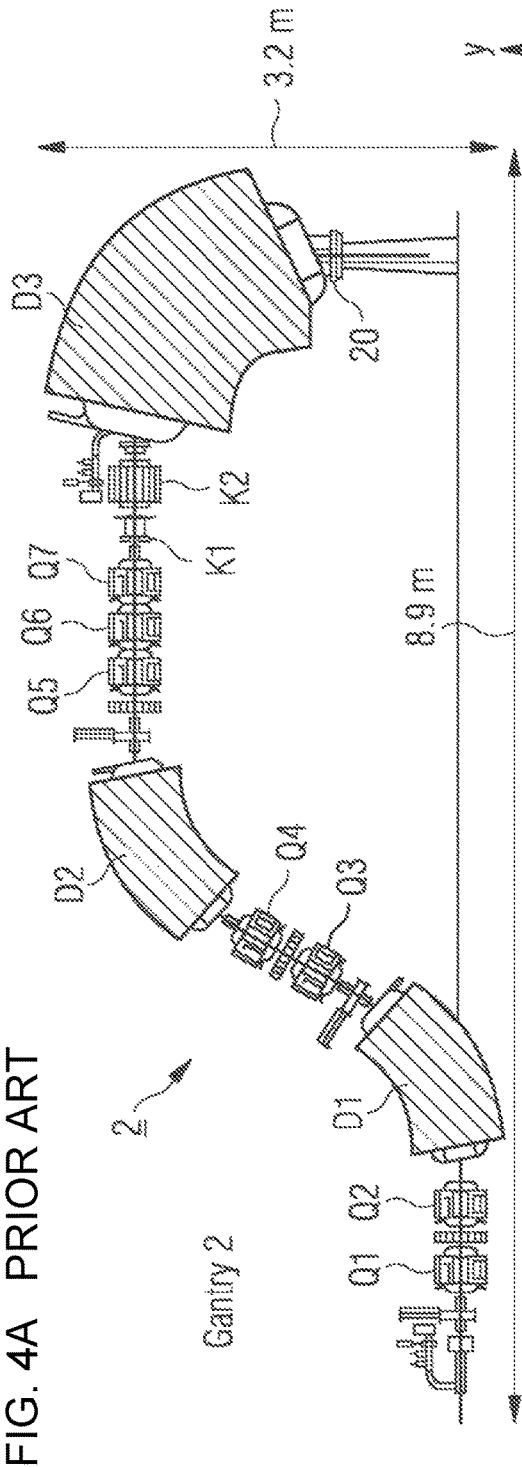
FIG. 4 schematically illustration of PSI Gantry 2 (top—FIG. 4A)and an example of a gantry with local achromaticity in each bending section and a degrader (bottom—FIG. 4B) according to the present invention with their dimensions.
Figure 4B:
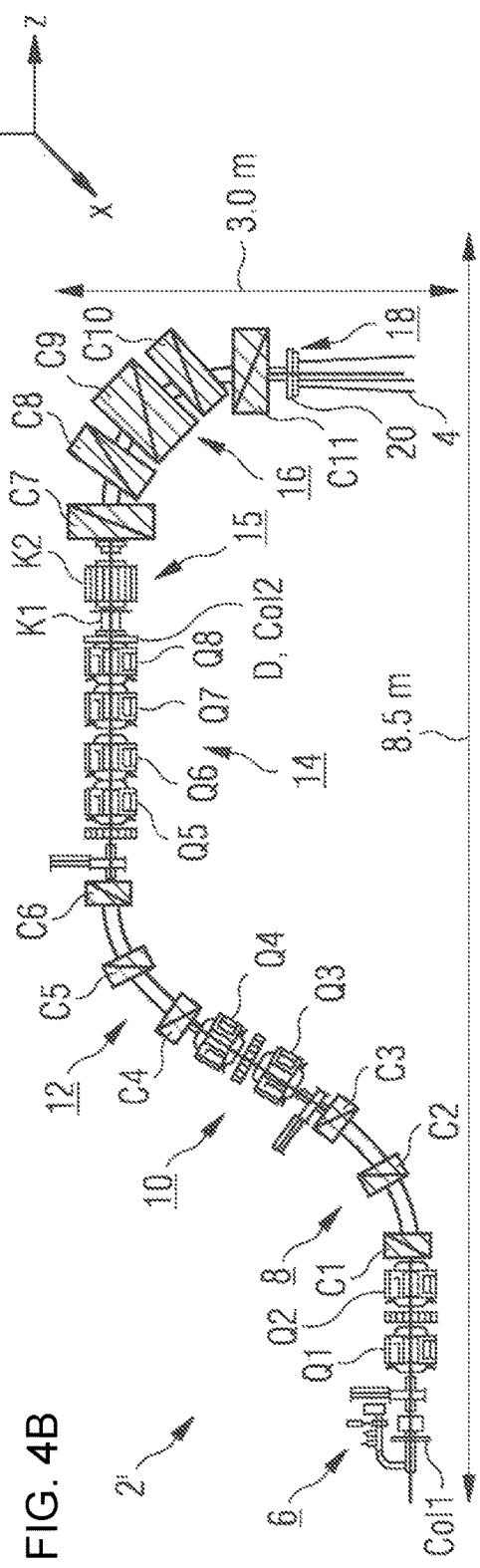
Figure 5:
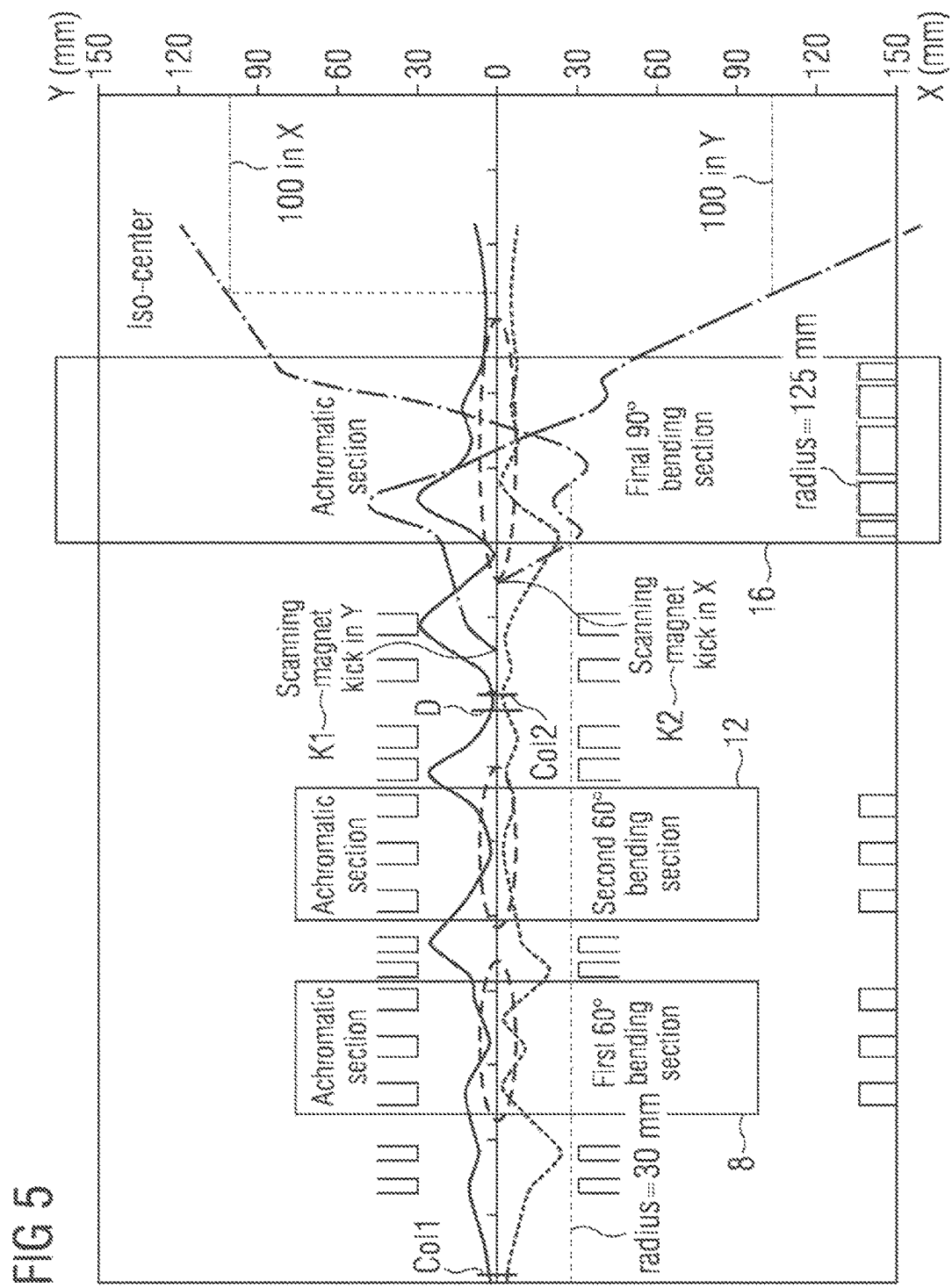
FIG. 5 the transport simulation result of the beam optics of the gantry shown in FIG. 4, bottom part.

The layout of PSI's Gantry 2 has been used as a template in the design of this version of the gantry discussed here. FIG. 4 shows the layout of a gantry 2' according to the present invention (bottom) compared with PSI "Gantry 2" (top). In FIG. 4 for the PSI "gantry 2", three dipole magnets D1, D2 and D3 and seven quadrupoles Q1 to Q7 and two kicker magnets K1, K2 are shown. In FIG. 4, bottom, for the new design of the gantry 2' quadrupole magnets Q1 to Q8 and combined function magnets (dipole and quadrupole) C1 to C11 and the scanning magnets K1 and K2 are provided. In both designs, there are two bending sections 8, 12 of 60° and one last bending section 16 of 90°. However, in the gantry 2' the bending sections 8, 12, 16 comprise several subsequent combined function magnets C1 to C11 with overlapping dipole and quadrupole fields. Additionally, the design contains eight g quadrupoles Q1 to Q8 before and between the bending sections (8, 12). Further, a first collimator Col1 and a second collimator Col2 have been added as well as a degrader D which is disposed upstream of the second collimator Col2. The gantry 2' as a whole is rotatable around the z-axis as shown in FIG. 4b.

Scanning is implemented upstream of the final last bending section 16, requiring a relatively large aperture of the final bend magnets C7 to C11. With the magnets C1 to C11 the size of the gantry 2 is approximately 3.0 m in radius and 8.5 m in length.

Following our invention it is considered to mount the degrader D before the last bending section 16 in the design of the gantry 2' (see below). To obtain a good beam transport the beam should have a small diameter when entering the degrader D. The first collimator Col1 is disposed at the coupling point 6. The round collimator aperture of this first collimator Col1 at the coupling point 6 at the entrance of the gantry 2' is imaged to the second collimator Col2 being disposed downstream of the degrader D between the second bending section 12 and the third bending section 16. The (1σ) beam size at this second collimator Col2 is 1.25 mm×1.25 mm. From this second collimator Col2 a point-to-point imaging is made to the iso-center, so that the beam spot size there is 2.5 mm×2.5 mm (at 1σ) in first-order.

As discussed above, most existing gantries are achromatic as a whole but usually the achromaticity is not restored within each individual bending section (global achromaticity). As a consequence the dispersion can become very large within the gantry. This limits the momentum acceptance of the globally achromatic system. In the example of the gantry design presented above, each bending section 8, 12, 16 is achromatic by itself ("local achromaticity"). The dispersion function never reaches a high value in that case. Using this feature, the gantry design presented here, has a momentum acceptance of >±10%. This means that without a change of the currents in the superconducting magnets, a beam with a momentum deviation of up to ±10% (corresponding to the energy deviation of almost ±20%) can still pass through the aperture of the gantry magnets and the vacuum pipe.

The advantage of the degrader D at this location is that the beam size is small, so that shifting (e.g. carbon) degrader plates into the beam trajectory, can be done within several milliseconds only. This would allow very fast energy changes.

In the design presented here the beam forms a waist at the position of the second collimator Col2, which is designed such that the beam divergence is high by strong focusing, so that the degrader D will not increase the beam divergence too strongly.

An alternative possibility in the design is another location of the scanning magnets.

The scanning magnets could be positioned within or behind the last bending section 16. A possible advantage could be that a smaller aperture of the magnets in the last bending section 16 can be used, without reducing the momentum acceptance.

The gantry 2' combines in a smart way existing beam handling methods enabling new options for the beam optics in a gantry. These include a strong dispersion suppression within each single bending section. The local dispersion suppression will keep the maximum value of dispersion low along the whole beam line of the gantry 2'. In the present invention, this property is used to accept a very large energy spread to enable the transport of an energy modulated beam without adjusting the bending field. This enables a very fast beam energy modulation, which is an important advantage in proton therapy.

The invention claimed is:

1. A movable gantry for delivery of a particle beam using beam scanning technique, the movable gantry comprising:
   an inlet section for an accelerated particle beam and having a plurality of quadrupole magnets;
   a first bending section having a plurality of dipole and quadrupole magnets for beam correction;
   a transfer section having a plurality of said quadrupole magnets for the beam correction and a degrader;
   a last beam bending section having a plurality of separate and/or combined dipole/quadrupole/higher order multipole magnets forming an achromatic section, wherein all said magnets of said achromatic section disposed downstream of said degrader, any dispersion in said achromatic section being suppressed so that the dispersion will have a momentum acceptance of more than ±5%;
   a scanning section having two separate or one combined fast deflection magnets that deflect the particle beam at an iso-center in a direction perpendicular to a beam direction to perform lateral scanning; and
   a beam nozzle section having a beam nozzle.

2. The gantry according to claim 1, further comprising a collimator or collimator system disposed downstream of said degrader.

3. The gantry according to claim 1, wherein said scanning section is disposed upstream or within or downstream of said last beam bending section.

4. The gantry according to claim 1, wherein said first bending section forms a further achromatic section or a combination of several achromatic sections.

5. The gantry according to claim 1, wherein the gantry is rotatable around a longitudinal axis.

6. The gantry according to claim 1, wherein the gantry is rotatable around a horizontal axis perpendicular to the direction of the particle beam entering the gantry.

7. The gantry according to claim 1,
   further comprising a second bending section having a plurality of said dipole and quadrupole magnets;
   wherein said first and second bending sections has further magnets for the beam correction;
   wherein said transfer section has further magnets for the beam correction; and
   wherein said nozzle section further has beam handling equipment selected from the group consisting of further beam degrading or modifying elements and beam quality related beam verifying elements.

* * * * *